United States Patent
Raj (10) Patent No.: US 7,901,949 B2
(45) Date of Patent: Mar. 8, 2011

(54) ASSAY

(75) Inventor: Balbir Raj, Bedford (GB)

(73) Assignee: Alere Switzerland GmbH, Zug (CH)

( * ) Notice: Subject to any disclaimer, the term of this patent is extended or adjusted under 35 U.S.C. 154(b) by 33 days.

(21) Appl. No.: 11/423,581

(22) Filed: Jun. 12, 2006

(65) Prior Publication Data

US 2007/0015290 A1  Jan. 18, 2007

Related U.S. Application Data (63) Continuation of application No. PCT/GB2004/005146, filed on Dec. 10, 2004.

(60) Provisional application No. 60/585,118, filed on Jul. 1, 2004.

(30) Foreign Application Priority Data

Dec. 12, 2003  (GB) .................................. 0328892.5

(51) Int. Cl.
*G01N 33/53* (2006.01)

(52) U.S. Cl. ........... 436/514; 435/4; 435/7.1; 435/287.1; 435/287.2; 435/810; 436/501; 436/518; 422/68.1; 422/50

(58) Field of Classification Search ............... 422/50, 422/56, 68.1; 435/4, 7.1, 287.1, 287.2; 436/501, 436/518

See application file for complete search history.

(56) References Cited

U.S. PATENT DOCUMENTS

| 5,296,347 | A | * | 3/1994 | LaMotte, III | ..................... 435/5 |
| 5,451,504 | A | | 9/1995 | Fitzpatrick et al. | |
| 5,874,216 | A | | 2/1999 | Mapes | |
| 6,037,127 | A | | 3/2000 | Ebersole et al. | |
| 6,352,862 | B1 | | 3/2002 | Davis et al. | |

(Continued)

FOREIGN PATENT DOCUMENTS

EP  0383619  8/1990

(Continued)

OTHER PUBLICATIONS

International Search Report for PCT/GB2004/005146.

(Continued)

*Primary Examiner* — Bao-Thuy L Nguyen
(74) *Attorney, Agent, or Firm* — Foley Hoag LLP (57) ABSTRACT

The present invention provides an assay kit for detecting an analyte of interest in a sample. The kit comprises a) a reporter species; b) a labelled species having first and second binding regions, wherein the first binding region is capable of binding to the analyte of interest and the second binding region is capable of binding to the reporter species; c) an immobilised species capable of binding to the first binding region of the labelled species; and d) immobilised capture reagent capable of binding to the reporter species. The arrangement is such that the sample is contacted with the labelled species, is then contacted with the immobilised species and is subsequently contacted with the immobilised capture reagent, the reporter species being added prior to exposure of the sample to the immobilised capture reagent. If no analyte is present in the sample, the labelled species becomes bound to the immobilised species and is therefore unable to bind to the immobilised capture reagent. If analyte is present in the sample, the analyte binds to the labelled species such that the labelled species is unable to bind to the immobilised species but can bind to the immobilised capture reagent via the reporter species, the presence of the analyte thus being determined by the presence of labelled species bound to the immobilised capture reagent via the reporter species.

13 Claims, 4 Drawing Sheets

U.S. PATENT DOCUMENTS

| | | | |
|---|---|---|---|
| 6,916,666 B1 * | 7/2005 | Mendel-Hartvig et al. | 436/518 |
| 7,026,002 B1 * | 4/2006 | Goerlach-Graw et al. | 426/514 |
| 7,241,628 B2 * | 7/2007 | Schaffler et al. | 436/518 |
| 2002/0142291 A1 | 10/2002 | Bauer et al. | |
| 2002/0182628 A1 * | 12/2002 | Dietz-Band et al. | 435/6 |
| 2003/0153096 A1 * | 8/2003 | Li et al. | 436/518 |
| 2007/0172963 A1 * | 7/2007 | Krauth et al. | 436/514 |

FOREIGN PATENT DOCUMENTS

| | | |
|---|---|---|
| EP | 0833157 B1 | 11/2002 |
| EP | 0962771 B1 | 4/2003 |
| EP | 0291194 B2 | 7/2003 |
| WO | WO-92/18868 | 10/1992 |
| WO | WO 95/27081 A | 10/1995 |
| WO | WO-98/57172 | 12/1998 |

OTHER PUBLICATIONS

Written Opinion of the International Searching Authority for PCT/GB2004/005146.

* cited by examiner

ASSAY

CROSS-REFERENCE TO RELATED APPLICATIONS

This application is a continuation of International Application No. PCT/GB2004/005146, filed Dec. 10, 2004, which is hereby incorporated herein by this reference. International Application No. PCT/GB2004/005146 claims the benefit of U.S. Provisional Application No. 60/585,118, filed Jul. 1, 2004 and also claims the benefit of GB application No. 0328892.5, filed Dec. 12, 2003, both of which are hereby incorporated herein by this reference.

FIELD OF THE INVENTION

The present invention relates to assay devices, in particular but not exclusively, lateral flow assay devices, and their use in detecting the presence or absence of an analyte, in particular but not exclusively, a hapten, in a sample.

BACKGROUND

Lateral flow immunoassay devices for the detection of the presence and/or amount of a hapten in a sample are known, such as disclosed by EP291194. Due to the small size of hapten species, sandwich capture reagent type binding reactions wherein capture reagents specifically bind at two different epitopes of the analyte are not possible. Instead a competition reaction is employed wherein analyte in the sample competes with another species, typically the same analyte, for a labelled capture reagent. Typically, the lateral flow carrier comprises a reagent zone containing particulate labelled reagent and a detection zone comprising an immobilised species downstream from the reagent zone. In the absence of analyte, labelled reagent binds at the detection zone giving rise to a detectable signal. In the presence of analyte in the sample, which is typically added upstream from the reagent zone, labelled reagent is able to bind preferentially with the analyte and thus is unable to bind at the detection zone. Thus, the signal formed at the detection zone decreases as the analyte concentration increases. For a semi-quantitative yes-no visual read test, presentation of the result in this way may lead to confusion or uncertainty for the user. In order to avoid this uncertainty, manufacturers of such immunoassays have gone to the extent of printing pictures onto each device of what positive and negative results should look like, to aid in interpretation of the result by the user. Typically, the users of such assays, for example for the detection of certain drugs of abuse, would be laboratory technicians. However, the increased use of drugs of abuse has led to an increased use of such tests by untrained individuals. Thus, the ease by which the result can be interpreted is of great importance.

U.S. Pat. Nos. 5,451,504 and 5,874,216 disclose immunoassay tests for the detection of haptens wherein the signal formed at the detection zone increases as the analyte concentration increases.

There is a need to provide alternative/improved methods for detecting the presence of an analyte in a sample, wherein the signal produced increases with an increase in analyte concentration.

SUMMARY

According to a first aspect, the invention provides an assay kit for detecting an analyte of interest in a sample, comprising:

a) a reporter species;
b) a labelled species having first and second binding regions, wherein the first binding region is capable of binding to the analyte of interest and the second binding region is capable of binding to the reporter species;
c) an immobilised species capable of binding to the first binding region of the labelled species; and
d) immobilised capture reagent capable of binding to the reporter species, the arrangement being such that the sample is contacted with the labelled species, is then contacted with the immobilised species and is subsequently contacted with the immobilised capture reagent, the reporter species being added prior to exposure of the sample to the immobilised capture reagent, wherein, if no analyte is present in the sample, the labelled species becomes bound to the immobilised species and is therefore unable to bind to the immobilised capture reagent, and wherein, if analyte is present in the sample, the analyte binds to the labelled species such that the labelled species is unable to bind to the immobilised species but can bind to the immobilised capture reagent via the reporter species, the presence of the analyte thus being determined by the presence of labelled species bound to the immobilised capture reagent via the reporter species.

The immobilised species may be provided in a trapping zone and the immobilised capture reagent may be provided in a separate detection zone, the sample moving from the trapping zone to the detection zone.

The labelled species may be provided in a reagent zone situated upstream of the trapping zone. Following application of the sample to the reagent zone, the labelled species may become mobilised in the sample and be able to bind to the analyte of interest (if present) in the sample and further be able to move to the trapping zone and subsequently to the detection zone. The reporter species, the labelled species, the immobilised species and the immobilised capture reagent may be provided on and/or in a substrate, which may be a lateral flow carrier.

The reporter species may be mobilisable, and may be present on the substrate upstream of the detection zone. In one embodiment, the reporter species is provided at or upstream from the reagent zone. In another embodiment, the reporter species is provided in the trapping zone.

The first and second binding regions of the labelled species may be capable of binding specifically to the analyte of interest and the reporter species, respectively, the immobilised species may be capable of binding specifically to the first binding region of the labelled species, and the immobilised capture reagent may be capable of binding specifically to the reporter species.

According to a second aspect, the invention provides a lateral flow carrier immunoassay device comprising:

a) a reagent zone having a mobilisable labelled species having first and second binding regions, wherein the first binding region is specific to the analyte of interest and the second binding region is specific to a reporter species;
b) a trapping zone situated at or downstream of the reagent zone comprising an immobilised analyte of interest to be detected;
c) a detection zone situated downstream of the trapping zone comprising an immobilised capture reagent specific for the reporter species and;
d) a mobilisable reporter species situated upstream from the detection zone.

According to a third aspect, the invention provides a method of detecting the presence of an analyte of interest in a sample, the method comprising:
  allowing the sample to contact a labelled species having first and second binding regions, wherein the first binding region is capable of binding to the analyte of interest and the second binding region is capable of binding to a reporter species;
  allowing the sample to contact immobilised species capable of binding to the first binding region of the labelled species;
  subsequently allowing the sample to contact immobilised capture reagent capable of binding to the reporter species;
  wherein the reporter species is added prior to contact of the sample with the immobilised capture reagent, and wherein, if no analyte is present in the sample, the labelled species binds to the immobilised species and therefore is unable to bind to the immobilised capture reagent via the reporter species, and wherein, if analyte is present in the sample, the analyte binds to the labelled species such that the labelled species is unable to bind to the immobilised species but can bind to the immobilised capture reagent via the reporter species, the presence of the analyte thus being determined by the presence of labelled species bound to the immobilised capture reagent via the reporter species.

The sample may be exposed to a trapping zone present on a substrate having the immobilised species, before being exposed to a detection zone on the substrate having immobilised capture reagent.

The method of the third aspect of the invention may comprise exposing the sample to a reagent zone on a substrate having the labelled species. The labelled species may be mobilised in the sample when the sample contacts the reagent zone, the mobilised labelled species then being able to bind to the analyte of interest (if present) in the sample.

The method of the third aspect of the invention may comprise the single step of adding the sample suspected of containing the analyte of interest to a substrate comprising a mobilisable reporter species, a mobilisable labelled species immobilised species and immobilised capture reagent. Alternatively the reporter species and/or the labelled species may be added to the sample prior to application to the substrate.

According to a further aspect, the invention provides for a method for the positive detection of a hapten wherein fluid sample is added to a lateral flow carrier whereupon analyte, if present, forms a first binding complex with the mobilisable-labelled species. The mobilisable labelled species, either prior or subsequent to forming the analyte complex also undergoes a specific binding reaction with the reporter species which subsequently permeates into the detection zone whereupon it is captured by the immobilised capture reagent specific for the reporter species. The labelled reagent present in the detection zone may then be determined or visualised to provide an indication of the presence of analyte.

In the absence of analyte, the mobilisable-labelled species forms a binding complex with the reporter species. This complex is subsequently captured by the trapping zone and is therefore unable to permeate into the detection zone.

According to a further aspect, the invention provides the use of an assay kit or device of the invention in the detection of an analyte in a sample.

The invention provides an assay kit or device for the detection of an analyte in a sample, wherein the signal produced increases proportionately with an increase in analyte concentration in the sample. The sample may be a fluid, such as a liquid, for example a bodily liquid taken from a subject, or may be a liquid derived from a solid. The assay or other reagents may be used to derive a liquid sample from a solid.

The assay kit or device may comprise a single continuous strip of material with separate zones positioned appropriately on the material so that the direction of flow of the sample is from the reagent zone (if present), to the trapping zone, and through to the detection zone. Alternatively, the assay device may comprise individual compartments designated to perform the defined functions of each of the reagent zone, trapping zone and detection zone and a means of transferring the product of each compartment to the next compartment. The zones may refer to individual sections of the same or different materials. The sections may partially or fully overlap each other such that sample is able to pass from one section to another. The mobilisable reagents may be provided on one or more sections of a material having good release characteristics (i.e. enabling the reagent to become resuspended in the sample and to permeate along or through the material) and the immobilised reagents may be provided on one or more sections having good binding characteristics. The sections may be treated prior to use to enhance or reduce the binding and/or their release characteristics. An example of a material having good release characteristics is glass fibre; an example of a material having good binding characteristics is nitrocellulose. Such treatments and materials are described in EP291194 and EP383619.

The lateral flow carrier of certain embodiments of the invention may be chosen from a suitable porous carrier such as nitrocellulose. Alternatively, any suitable material which permits the movement of a sample through a trapping zone and detection zone may be used. Additionally, the lateral flow carrier material may be supported by a strengthening solid backing material to increase the handling strength of the device. The carrier may also consist of more than one material arranged so as to be in fluidic contact with each other.

Alternatively the lateral flow carrier could be a microfluidic carrier having one or more capillary pathways.

Alternatively, the substrate of the assay kit of the invention may be one or a series of layers or columns comprising immobilised and optional mobilisable reagents. In one embodiment, the immobilised species and immobilised capture reagent are arranged such that the sample and the labelled species are caused to contact the immobilised species, and subsequently the immobilised capture reagent, wherein the reporter species is added prior to contact with the immobilised capture reagent The assay kit of the invention may also include a fluid sink and/or a sample receiving member, as well a control zone situated downstream from the detection zone as disclosed by U.S. Pat. No. 6,352,862. Accordingly, in a further embodiment of the assay kit of the invention, the assay kit comprises a control marker, which may be mobilisable, situated upstream of the immobilised analyte and a control zone situated downstream of the immobilised capture reagent, the control zone comprising an immobilised capture reagent capable of binding to the control marker. The control marker may be able to permeate through the trapping zone and the detection zone with the sample to reach the control zone, where it is bound by the immobilised capture reagent. The detection of the control marker at the control zone confirms that the sample has successfully permeated through the assay kit, thus providing the user with a positive signal that the test has been completed successfully. The labelled species may also function as the control marker. A signal may be produced at the control zone by any suitable method. In one embodiment, the control zone may comprise immobilised receptor for a mobilisable control marker which may be present at any point in the assay device upstream of the control zone so long as the detection of the control marker can be distinguished from the detection of the analyte. As the sample moves along the assay device through the trapping zone and the detection zone, it carries with it the mobilisable control marker. Alternatively, the control zone may comprise an immobilised anhydrous substance which is induced to change colour when the fluid sample reaches the control zone. Further alternative methods of providing a positive signal at the control zone may be included in an assay device of the present invention.

The assay kit or device of the present invention may additionally be incorporated with a housing which may be fluid impermeable, such as disclosed by EP291194.

In one embodiment, a lateral flow immunoassay device is provided which is contacted with a sample, typically at one end of the device. The sample flows through the porous flow carrier material to first the reagent zone (if present), then on to the trapping zone, and further on to the detection zone by capillary action. Alternatively, the sample may be urged to move through the successive zones of an assay device of the invention by other forces such as gravity, centrifugal force, agitation, etc.

The reagent zone of certain embodiments of the invention comprises a mobilisable labelled species having a first and a second binding region, wherein the first binding region is specific for the analyte of interest, and the second binding region is specific for a reporter species. The mobilisable labelled species may be deposited on the substrate at the reagent zone by a number of methods known to one of skill in the art so that the species remains fixed at the reagent zone prior to the addition of the sample. On addition of the sample, the mobilisable species becomes mobile, being carried by the sample through the remainder of the substrate. The mobile labelled species is free to move within the sample, and is able to interact with, and bind to both the reporter species and the analyte (if present in the sample).

A mobilisable reporter species may be present within the reagent zone. A known concentration of the reporter species may be applied to the substrate of the invention by methods known to one of skill in the art. In certain embodiments, the reporter species is therefore present in or on the substrate prior to application of the sample, and becomes mobilised by the addition of the sample to the substrate. The reporter species may be chosen from a species that will not already be present in the sample of interest. In one embodiment, the reporter species is chosen such that it does not interfere with the binding events of the analyte of interest. Similarly, the analyte of interest may not interfere with the binding events at the detection zone. In one embodiment of the invention, the reporter species is ovalbumin-FITC conjugate.

The first and second binding regions of the labelled species may be specific for either analyte of interest and the reporter species respectively, with minimal or no specificity (such as undetectable above background) for the other analyte. The binding regions may comprise any molecule capable of binding specifically with an intended target molecule and not capable of binding to any other molecule at detectable levels. Where the reporter species is a species having a single epitopic site such as a hapten, the reporter species may be conjugated to a carrier such as BSA or ovalbumin, which itself does not interfere with the assay. The reporter species may be conjugated to a suitable carrier molecule using standard conjugation methods known to the person skilled in the art.

Where the reporter species is larger, enabling binding reactions to take place at different epitopic sites, such epitopic sites being either the same or different, the reporter species may be used without necessarily having to conjugate it to a carrier.

Each binding region of the labelled species may be a specific binding region that is able to specifically bind with the species of interest to form a specific binding pair. Examples of specific binding pairs include an antibody and antigen where the antigen may be a peptide sequence, complementary nucleotide or peptide sequences, polymeric acids and bases, dyes and protein binders, peptides and specific protein binders, enzymes and cofactors, and effector and receptor molecules, where the term receptor refers to any compound or composition capable of recognising a particular or polar orientation of a molecule, namely an epitopic or determinant site.

Reference to an antibody includes but is not limited to, polyclonal, monoclonal, bispecific, humanised and chimeric antibodies, single chain antibodies, Fab fragments and F(ab')$_2$ fragments, fragments produced by a Fab expression library, anti-idiotypic (anti-Id) antibodies, and epitope-binding fragments of any of the above. Portions of antibodies include Fv and Fv' portions. Fv portions can be modified to produce a synthetic construct known as a single chain Fv (scFv) molecule. This includes a peptide linker covalently joining $V_h$ and $V_1$ regions, which contributes to the stability of the molecule. Antibodies can be naturally-occurring antibodies, e.g., monoclonal antibodies obtained by the method of Koehler and Milstein and polyclonal antibodies obtained, for example, by injection of an antigen into an animal. Antibodies can also be partially or fully humanised. Other synthetic constructs that can be used include Complementarity Determining Regions (CDR) peptides. These are synthetic peptides comprising antigen-binding determinants. Peptide mimetics may also be used. These molecules are usually conformationally restricted organic rings that mimic the structure of a CDR loop and that include antigen-interactive side chains.

The labelled species capable of binding both the analyte of interest and the reporter species could be for example a direct particulate label co-sensitised with a first specific binding agent having specificity for an analyte or analyte analogue and a second specific binding agent having specificity for the reporter species. Examples of co-sensitised species are disclosed in EP833157. Alternatively, the mobilisable-labelled species could be a labelled bispecific capture species having two binding regions specific to the analyte and the reporter species. Examples of bispecific capture reagents are given in EP962771.

The label can be any suitable entity and may be a direct particulate label such as a metallic sol such as gold sol or for example organic particles such as polyurethane or latex which have been loaded with a suitable dye, including fluorescent dyes.

The label may be any suitable label capable of being detected and quantified. Additional examples of suitable labels include particles such as carbon black, enzymes capable of reacting to produce a coloured reaction product, such as horseradish peroxidase and alkaline phosphatase, molecules capable of producing detectable light such as bioluminescence, chemiluminescence, phosphorescence and fluorescence, or any other label known to one of skill in the art.

The trapping zone of the present invention may be situated downstream of the reagent zone relative to the direction of flow of the sample, in those embodiments comprising a reagent zone. The trapping zone comprises the immobilised species which may be fixedly attached to the substrate of the assay device, and this immobilised species binds to any labelled species whose first binding region is not already bound to the analyte of interest in the sample. In this way, the trapping zone prevents any labelled species which is not bound to the analyte of interest in the sample from progressing to the detection zone, and thus prevents the occurrence of false positive results (the production of a signal at the detection zone when there is in fact no analyte of interest present in the fluid sample). Any labelled species bound to analyte of interest in the sample (and which will also bind to the reporter species) will pass through the trapping zone and progress to the detection zone. Thus, there is no competition reaction between the analyte and a labelled species for binding sites at the trapping zone, and any analyte present in the sample will directly result in the progress of the labelled species to the detection zone.

The immobilised species may be the analyte of interest or an analogue thereof. Analogues of the analyte of interest include the analogous molecule from a related species of animal, where such an animal exists, or molecules synthesized to structurally mimic the analyte, or a particular binding region of the analyte.

The immobilised species may be attached to the substrate at the trapping zone by any means known to one of skill in the art. The immobilised species may be attached directly, or may be attached to a supporting molecule which is itself immobilised in the trapping zone. Alternatively, the immobilised species may be immobilised on a supporting material, such as a solid plastic sheet, which is held in fluidic contact with the flow carrier material. Alternatively, the immobilised species may be attached to the surface of the assay material which is in contact with the sample as it moves through the device. For example, when the immunoassay device is a microfluidic device, the immobilised species may be attached to the internal surfaces of the capillary pathways which carry the sample through the device.

In practice, the capture efficiency of the trapping zone will be less than 100% and thus, even in the absence of analyte in the fluid sample, not all of the reporter species-labelled reagent binding complex will necessarily be captured by the trapping zone and will therefore permeate into the detection zone. However, in order to avoid the appearance of a false positive, the levels of reporter species present in the assay device may be chosen to be at a level such that when sample without analyte is added to the device, labelled reagent will not be observable at the detection zone. The amount of reporter species added may vary depending upon the type of lateral flow carrier and how it is treated. The optimum amount is most easily determined by routine experimentation. The detection zone may be situated downstream of the trapping zone with respect to the direction of the flow of the sample, and may comprise immobilised capture reagent capable of binding the reporter species. The immobilised capture reagent may bind to the reporter species, thus immobilising the labelled species only when the reporter species is bound to the labelled species. Thus, a positive signal will be produced at the detection zone only when analyte present in the sample binds to the labelled species, which also binds the reporter species, which is in turn bound at the detection zone. In the absence of analyte in the sample, the reporter species will still progress to the detection zone where it will be bound to the immobilised capture reagent, yet no signal will be produced due to the absence of labelled species from the detection zone.

In one embodiment of the invention, the assay device comprises a trapping zone and a detection zone. Prior to adding the sample to the device, the sample may be mixed with suitably buffered solution comprising a labelled species having first and second binding regions, wherein the first binding region is capable of binding to the analyte of interest and the second binding region is capable of binding to a reporter species, and, optionally, a reporter species. The solution may be suitably buffered to prevent any hindrance of the binding interactions which may occur between the analyte, the labelled species, and the reporter species. The sample may be mixed with the buffered solution for a suitable time to allow any binding reaction between the analyte (if present) in the sample, the labelled species and the reporter species to occur. After mixing, the sample may be added to the assay device at a point upstream of the trapping zone. The sample then passes through first the trapping zone, and then the detection zone by any means as described above. Thus, the initial binding interaction between the analyte, the labelled species and the reporter species may take place prior to the addition of the sample to the assay device.

The analyte of interest may be chosen from any species capable of undergoing a binding event with the first binding region of the labelled species. The assay device according to the invention is suitable for the detection of analytes including small molecules such as haptens. Haptens may be defined as small antigenic determinants capable of eliciting an immune response only when coupled to a carrier. Haptens may bind to antibodies but by themselves cannot elicit an antibody response, for example by injection of the hapten into the body of an animal. Non-limiting examples of haptens include amphetamine based drugs of abuse such as MDA(3, 4-methylenedioxyamphetamine), MDMA also known as "Ecstasy" (3,4-methylenedioxy-N-methylamphetamine), MDEA(3,4-methylenedioxy-N-ethylam phetamine), BDB (3,4-methylenedioxyphenyl-2-butanamine), MBDB(3,4-methylenedioxyphenyl-N-methylbutanamine), and MDPA (3,4-methylenedioxy-N-propylamphetamine); opiates such as morphine and codeine, as well as their synthetic analogues which includes heroin, hydromorphone, hydrocodone, oxycodone and oxymorphone; lysergic acid diethylamide (LSD) as well as metabolites thereof, tetrahydrocannabinol and cocaine; toxic drugs such as diazepam, nicotine, acetaminophen, caffeine, risperidone, phenobarbitol; hormones such as progesterone, estradiol and metabolites thereof, testosterone; pesticides; dyes such as fluorescein isothiocyanate, Texas red and so on.

In the present invention, the term "bodily liquid" includes all liquids that can be obtained from a mammalian body, including, for example, blood, plasma, urine, lymph, gastric juices, bile, serum, saliva, sweat, interstitial fluid and spinal and brain fluids. Depending upon the analyte of interest, other fluid and liquid samples may be contemplated such as ones from industrial, environmental or agricultural sources. Furthermore, the bodily liquids may be either processed (e.g., serum) or unprocessed. The sample may be pre-treated if necessary to obtain and/or release the analyte of interest and the treatment process may involve treating a solid sample to yield a liquid sample containing analyte of interest. Methods of obtaining a bodily liquid sample from a subject are known to those skilled in the art.

Preferred features of each aspect of the invention are as for each of the other aspects mutatis mutandis. The prior art documents mentioned herein are incorporated to the fullest extent permitted by law.

EXAMPLE

Reference is made to the accompanying drawings in which.

DETAILED DESCRIPTION OF THE INVENTION

Example

Figure 1:
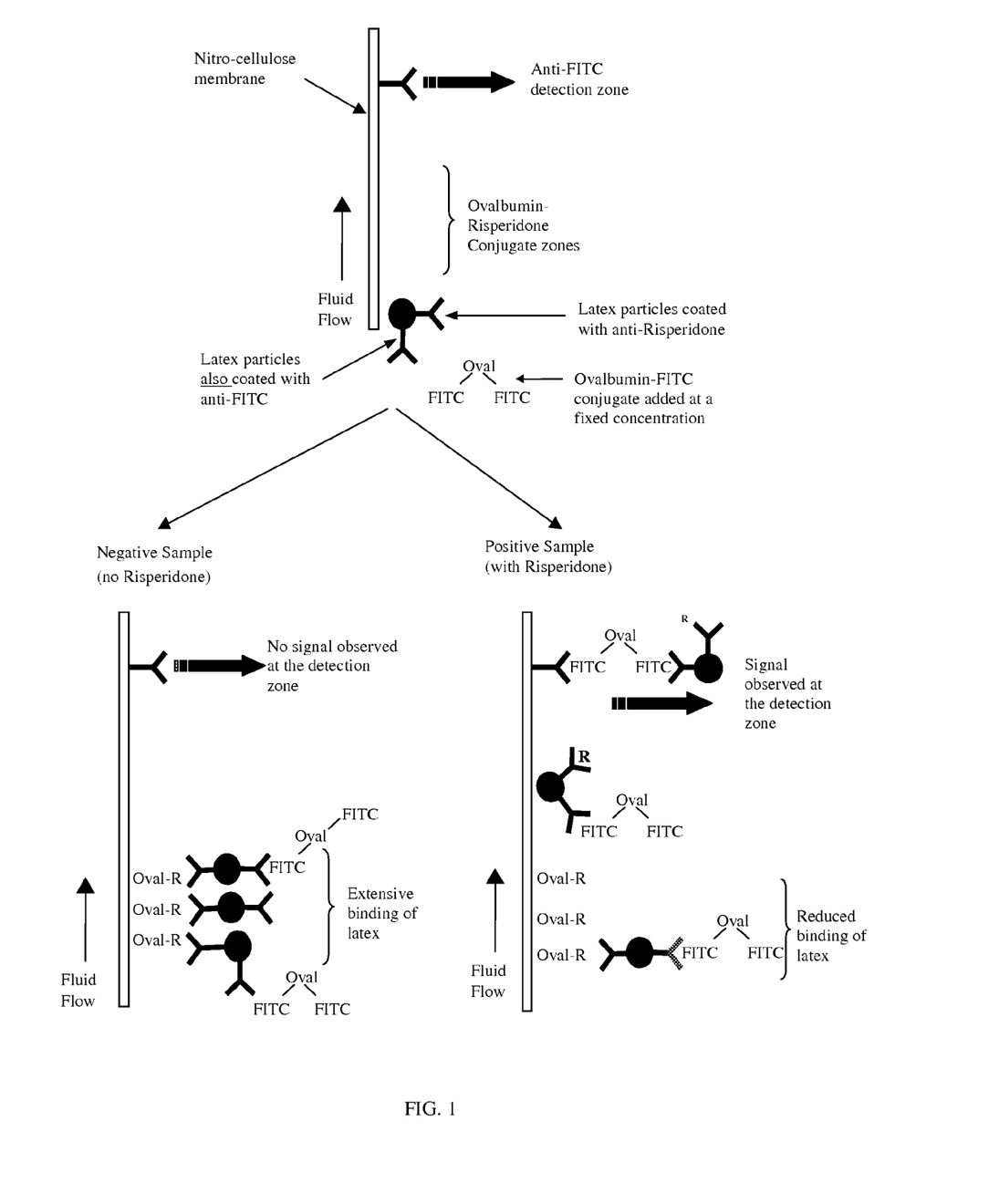
FIG. 1 illustrates one assay in accordance with the present invention designed for the detection of Risperidone, including an illustration of the outcome of the assay when a negative sample and positive sample is tested.

The features and advantages of the present invention may be more fully understood by reference to the following example, though it should be appreciated that the following example is only a specific embodiment of the invention, and that the invention should not be construed as being limited to the specific features of the specific embodiment described below. The example describes a positive read hapten assay for the anti-psychotic, Risperidone. In this example the reporter species is FITC (fluorescein-5-isothiocyanate, isomer 1) conjugated to an ovalbumin carrier. Various experiments were carried out to ensure that the anti-FITC antibody did not bind to Risperidone and that the anti-Risperidone antibody did not bind significantly to FITC. FIG. 1 provides a schematic diagram of the exemplified hapten assay, including the outcome when a positive and negative sample is tested.

Anti-FITC Antibodies

Supplied by Fitzgerald Inc. Concord Mass., USA (clones M25285, M25286, M49209). Following preliminary screening, clone M25286 was selected for use in these experiments.

Preparation of Ovalbumin-FITC Conjugate 10 mgs of FITC (Molecular Probes, USA) was mixed with 1 ml of dimethyl sulphoxide, (DMSO), (Aldrich Chemicals). Ovalbumin, (Sigma Chemical Co.) was prepared at 5 mg/ml in 50 mM carbonate buffer pH 9.3. A range of reaction ratios of ovalbumin to FITC was prepared, (ranging from 1:10 up to 1:40). The reactions were left overnight at room temperature wrapped in foil and purified the following morning by gel filtration, (PD10 column equilibrated with phosphate buffered saline, PBSA). All conjugates were diluted 1:100 in PBSA and characterised by UV/Visible scanning. The following incorporation ratios of Ovalbumin to FITC were produced: 1:2.5, 1:3.9, 1:3.8 and 1:2.6. Conjugate OBB02 was selected for use in these experiments having an incorporation ratio of 1:3.9

Preparation of the Ovalbumin-Risperidone Conjugate

Stock solutions of Risperidone, N-hydroxysuccinimide (Sigma), and 1-ethyl-3 (3 dimethylaminopropyl) carbodimide.HCl (Sigma), were prepared in dry dimethylformamide (DMF), (ROMIL). A solution of ovalbumin (Sigma) was prepared in 0.1M sodium phosphate buffer pH 7.

An activation mixture of Risperidone, N-hydroxysuccinimide and 1-ethyl-3(3 dimethylaminopropyl) carbodimide.HCl, (at a ratio of 1:1:1) was prepared in a glass bijou and left shaking at room temperature for ~2 hours. The above activation mixture was added dropwise to the solution of ovalbumin and left stirring on a magnetic stirrer overnight at room temperature. The amounts of the above reagents were selected to produce a reaction ratio of 25:1, (Risperidone to Ovalbumin). This ratio was selected in order to increase conjugation efficiency, however to reduce the possibility of precipitation.

The following morning the conjugate was purified by size exclusion chromatography using a PD 10 column, (Amersham Biosciences). Once applied to the column, the conjugate was eluted off in phosphate buffered saline (plus sodium azide) pH 7, (Sigma). Characterisation of the conjugate by HPLC produced an incorporation ratio of 6.8:1, (Risperidone to ovalbumin).

Preparation of the Lateral Flow Carrier

Reagents were dosed onto Mylar backed nitro-cellulose membrane, (8 µm Schleicher & Schuell, code C10888-1), using a pen linked to a metered pump and syringe in accordance with the methods disclosed by EP291194. The membrane was prepared with 3 zones of ovalbumin-Risperidone conjugate, (Risperidone 009, 2.39 mg/ml). The first zone was positioned 8.5 mm from the base of the test strip with subsequent zones separated 1.5 mm downstream from this. Anti-FITC, clone M25286, (2.5 mg/ml) was deposited as a single zone, 16 mm from the base of the strip, (viewing zone). Following deposition, the membrane was dried at 55° C. for 5 minutes and blocked in 1% (w/v) Polyvinyl alcohol (PVA) (Airvol 9K 18034004) plus 3% (w/v) sucrose, (BDH Analar K30139086 236). The blocking solution was allowed to chromatograph through the membrane until the membrane was saturated. Once saturated, the membrane was dried at 75° C. for 5 minutes.

Preparation of Latex Particles Coated in Anti-Risperidone and Anti-FITC

Duke Scientific blue latex, (CB 1615) (400 nm diameter) was coated at 0.5% (w/v) solids in a mixture containing anti-Risperidone, (100 ug/ml, clone 6352:1) as well as anti-FITC, (25 ug/ml, clone M25286). After incubation at room temperature for 60 minutes, the latex particles were blocked in 20 mg/ml BSA, (bovine serum albumin, Intergen Type H7 N21207) for 30 minutes at room temperature. Once prepared the particles were washed and exchanged into drying buffer, (100 mM borate pH 8.5 containing 6.5% BSA and 20% sucrose, (w/v)).

Deposition of Reagents onto Whatman Glass Fibre Material.

Figure 2:
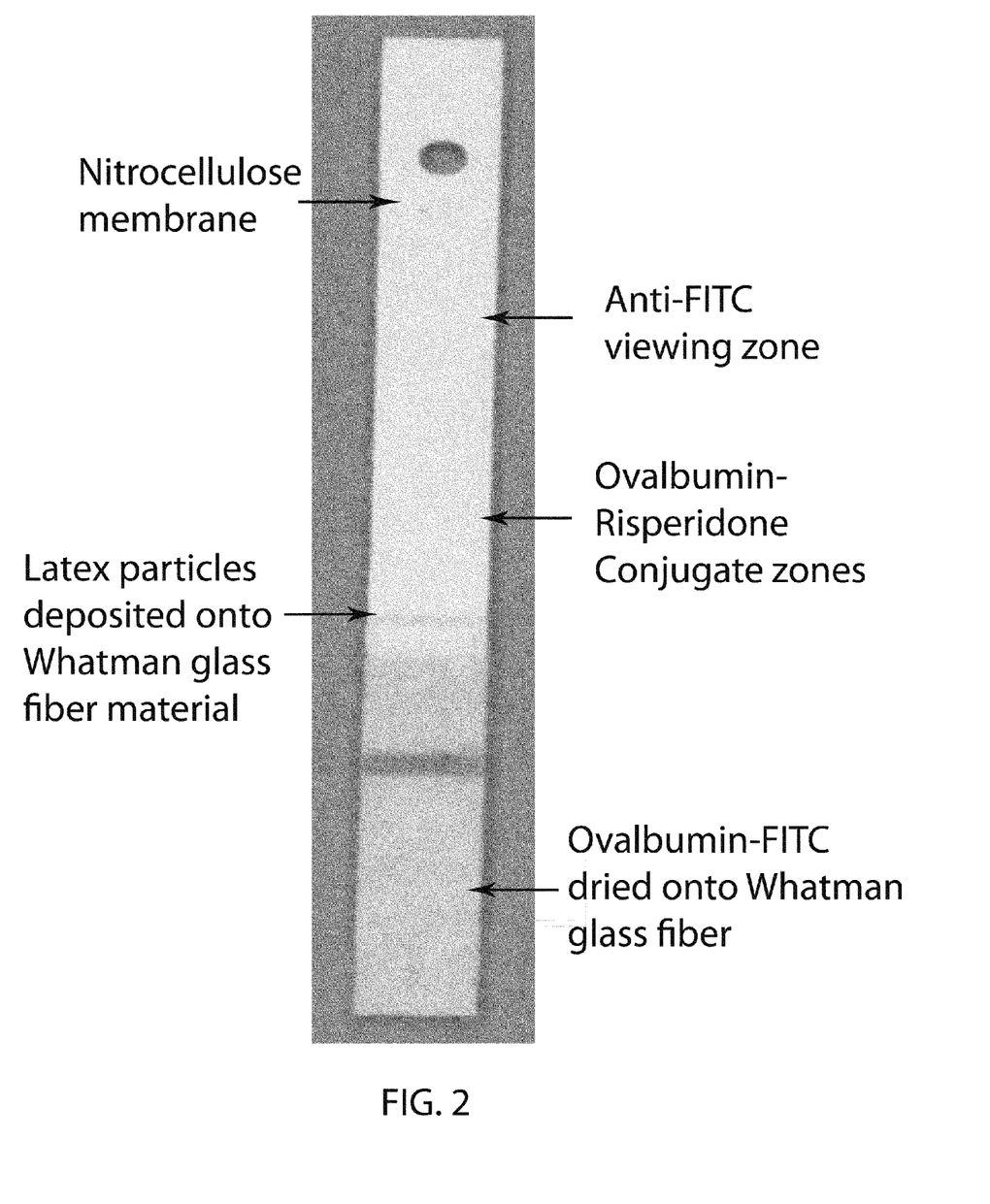
FIG. 2 displays an assay device of the invention, comprising a section of Whatman glass fibre material attached by lamination to a strip of nitro-cellulose membrane.

Latex particles coated in anti-Risperidone and anti-FITC above were deposited as a single line onto Whatman glass fibre carrier material, (in drying buffer). A Hamilton syringe and pump connected to an X-Y plotter was used to deposit the latex as a line on the carrier, (0.23 uls/mm). In addition, ovalbumin-FITC conjugate OBB02 was prepared at a 1:20 dilution in drying buffer and deposited as a separate line onto the same glass fibre material by Hamilton pump and syringe, (0.23 uls/mm). The Whatman glass fibre material was attached by lamination to nitro-cellulose membrane containing ovalbumin-Risperidone conjugate as well as the anti-FITC detection zone to produce the assay device as shown in FIG. 2.

Testing of the Devices

Risperidone standards were prepared from a stock of 1.18 mg/ml Risperidone by dilution in a pool of Risperidone negative urine. The assay devices as constructed were placed in a plastic casing such that ~3 mm of the Whatman glass fibre was capable of being held in a pool of Risperidone standard. The devices were held vertically in aliquots of 300 µl of Risperidone standards, prepared above, for a period of five minutes at room temperature.

After five minutes had elapsed, the devices were dried at room temperature. Signal intensity at the detection zone was quantified optically using a Persona™ monitor (sold by Unipath Ltd).

Figure 3:
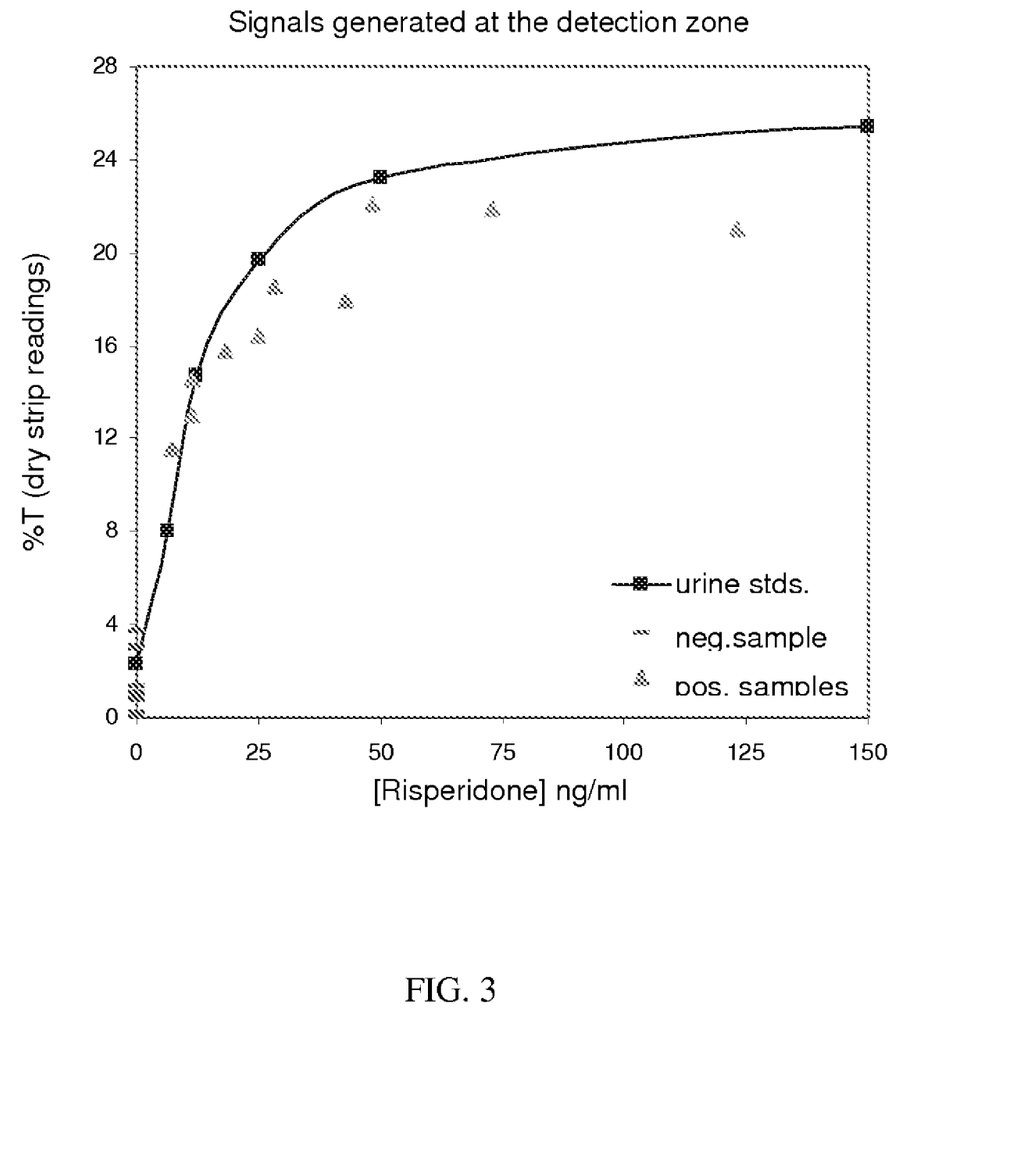
FIG. 3 illustrates the results of patient samples tested for the presence of Risperidone compared with standard Risperidone measures.

Various patient samples were tested and results shown in FIG. 3.

Figure 4:
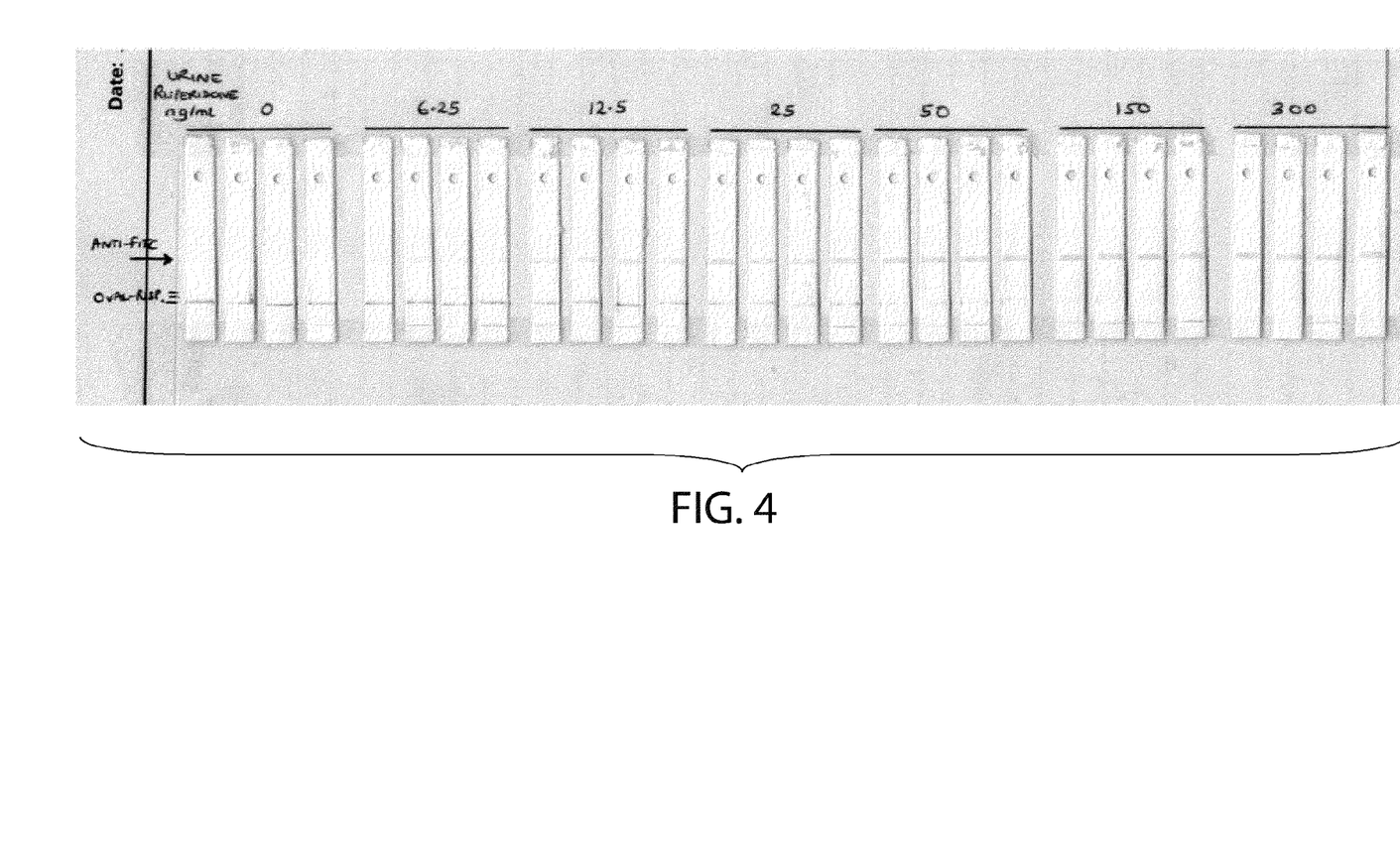
FIG. 4 shows various assay devices in accordance with the invention after testing with standard Risperidone measures.

FIG. 4 shows various assay devices strips after testing with urine Risperidone standards. These test strips clearly show how signal is depleted on the ovalbumin-Risperidone conjugate zones as the level of Risperidone in the urine rises. Conversely, the intensity of signal at the detection zone increases with increasing Risperidone concentration producing a positive response.

I claim:

1. A lateral flow immunoassay device for the detection of an analyte of interest in a liquid sample, comprising:
   a lateral flow test strip, the test strip in a dry state comprising:
   a) a mobilisable reporter species;
   b) a reagent zone having a mobilisable labelled species comprising a visually detectable label and, bound thereto, first and second binding agents, wherein the first binding agent is specific to the analyte of interest and the second binding agent is specific to the reporter species, wherein binding of the mobilisable labelled species and the reporter species forms a detectable complex;
   c) a trapping zone situated at or downstream of the reagent zone comprising an immobilised analyte of interest or a derivative of the analyte; and
   d) a detection zone situated downstream of the trapping zone comprising an immobilised capture reagent capable of binding the detectable complex of the reporter species and the mobilisable labelled species;
   wherein the mobilisable reporter species is situated upstream from the detection zone.

2. The device according to claim 1, further comprising:
   a mobilisable control marker situated upstream of the detection zone; and
   a control zone situated downstream of the detection zone comprising an immobilised capture reagent capable of binding the control marker.

3. The device according to claim 1, wherein the analyte of interest is a hapten.

4. The device according to claim 3, wherein the hapten comprises an amphetamine-based drug of abuse.

5. A device according to claim 4, wherein the hapten comprises at least one of MDA (3,4-methylenedioxyamphetamine), MDMA also known as "Ecstasy" (3,4-methylenedioxy-N-methylamphetamine), MDEA (3,4-methylenedioxy-N-ethylam phetamine), BDB (3,4-methylenedioxyphenyl-2-butanamine), MBDB (3,4-methylenedioxyphenyl-N-methylbutanamine), and MDPA (3,4-methylenedioxy-N-propylamphetamine).

6. The device according to claim 3, wherein the hapten comprises at least one of an opiate, morphine, codeine, heroin, hydromorphone, hydrocodone, oxycodone, and oxymorphone.

7. The device according to claim 3, wherein the hapten comprises at least one of lysergic acid diethylamide (LSD) and metabolites thereof.

8. The device according to claim 3, wherein the hapten comprises tetrahydrocannabinol.

9. The device according to claim 3, wherein the hapten comprises cocaine.

10. The device according to claim 3, wherein the hapten comprises at least one of diazepam, nicotine, acetaminophen, caffeine, risperidone, and phenobarbitol.

11. The device according to claim 3, wherein the hapten comprises at least one of a hormone, progesterone, estradiol and metabolites thereof, and testosterone.

12. The device according to claim 3, wherein the hapten comprises a pesticide.

13. The device according to claim 3, wherein the hapten comprises at least one of a dye, fluorescein isothiocyanate, and Texas Red.

* * * * *